United States Patent
Retsina et al.

(10) Patent No.: US 11,155,846 B2
(45) Date of Patent: Oct. 26, 2021

(54) METHODS FOR REDUCING CONTAMINATION DURING ENZYMATIC HYDROLYSIS OF BIOMASS-DERIVED CELLULOSE

(71) Applicant: API Intellectual Property Holdings, LLC, Minnetrista, MN (US)

(72) Inventors: Theodora Retsina, Atlanta, GA (US); Gonçalo Pereira, Campinas (BR); Vesa Pylkkanen, Atlanta, GA (US)

(73) Assignee: GranBio Intellectual Property Holdings, LLC, Atlanta, GA (US)

( * ) Notice: Subject to any disclaimer, the term of this patent is extended or adjusted under 35 U.S.C. 154(b) by 0 days.

(21) Appl. No.: 15/943,754

(22) Filed: Apr. 3, 2018

(65) Prior Publication Data
US 2019/0367958 A1 Dec. 5, 2019

Related U.S. Application Data

(62) Division of application No. 15/062,155, filed on Mar. 6, 2016, now abandoned.

(60) Provisional application No. 62/129,468, filed on Mar. 6, 2015.

(51) Int. Cl.
*C12P 19/02* (2006.01)
*C12P 19/14* (2006.01)
*C12P 7/10* (2006.01)

(52) U.S. Cl.
CPC ............... *C12P 19/02* (2013.01); *C12P 7/10* (2013.01); *C12P 19/14* (2013.01); *C12P 2201/00* (2013.01); *C12P 2203/00* (2013.01); *Y02E 50/16* (2013.01)

(58) Field of Classification Search
None
See application file for complete search history.

(56) References Cited

FOREIGN PATENT DOCUMENTS

WO WO 2014/193763 * 12/2014

OTHER PUBLICATIONS

Wang et al., "Lignosulfonate-mediated cellulase adsorption: enhanced enzymatic saccharification of lignocellulose through weakening nonproductive binding to lignin", Biotechnology for Biofuels, 2013, 6:156.*

* cited by examiner

*Primary Examiner* — Suzanne M Noakes
(74) *Attorney, Agent, or Firm* — O'Connor & Company; Ryan P. O'Connor

(57) ABSTRACT

Some variations provide a method of enzymatically converting biomass-derived cellulose to glucose, comprising exposing the biomass-derived cellulose to (i) cellulase enzymes, to hydrolyze the cellulose to glucose; and (ii) an external sulfur-containing compound, to deter bacterial and/or yeast contamination during cellulose hydrolysis. In some embodiments, the sulfur-containing compound includes sulfur dioxide or lignosulfonates. When the sulfur-containing compound includes lignosulfonates, the lignosulfonates may also function as an enzyme surfactant to assist hydrolysis, in addition to deterring bacterial and/or yeast growth/contamination. This method may be applied to cellulose-rich solids obtained from the AVAP® fractionation process, the GREEN POWER+® pretreatment process, or any other source of cellulose-rich solids.

9 Claims, No Drawings

METHODS FOR REDUCING CONTAMINATION DURING ENZYMATIC HYDROLYSIS OF BIOMASS-DERIVED CELLULOSE

PRIORITY DATA

This patent application is a divisional application of U.S. patent application Ser. No. 15/062,155 filed on Mar. 6, 2016, which claims priority to U.S. Provisional Patent App. No. 62/129,468 filed on Mar. 6, 2015, each of which is hereby incorporated by reference herein.

FIELD

The present invention generally relates to fractionation processes for converting biomass into cellulose-rich solids, and enzymatic conversion of the cellulose to glucose.

BACKGROUND

Biomass refining (or biorefining) is becoming more prevalent in industry. Cellulose fibers and sugars, hemicellulose sugars, lignin, syngas, and derivatives of these intermediates are being used by many companies for chemical and fuel production. Indeed, we now are observing the commercialization of integrated biorefineries that are capable of processing incoming biomass much the same as petroleum refineries now process crude oil. Underutilized lignocellulosic biomass feedstocks have the potential to be much cheaper than petroleum, on a carbon basis, as well as much better from an environmental life-cycle standpoint.

Lignocellulosic biomass is the most abundant renewable material on the planet and has long been recognized as a potential feedstock for producing chemicals, fuels, and materials. Lignocellulosic biomass normally comprises primarily cellulose, hemicellulose, and lignin. Cellulose and hemicellulose are natural polymers of sugars, and lignin is an aromatic/aliphatic hydrocarbon polymer reinforcing the entire biomass network. Some forms of biomass (e.g., recycled materials) do not contain hemicellulose.

Sugars (e.g., glucose and xylose) are desirable platform molecules because they can be fermented to a wide variety of fuels and chemicals, used to grow organisms or produce enzymes, converted catalytically to chemicals, or recovered and sold to the market. To recover sugars from biomass, the cellulose and/or the hemicellulose in the biomass must be hydrolyzed into sugars. This is a difficult task because lignin and hemicelluloses are bound to each other by covalent bonds, and the three components are arranged inside the fiber wall in a complex manner. This recalcitrance explains the natural resistance of woody biomass to decomposition, and explains the difficulty to convert biomass to sugars at high yields.

Fractionation of biomass into its principle components (cellulose, hemicellulose, and lignin) has several advantages. Fractionation of lignocellulosics leads to release of cellulosic fibers and opens the cell wall structure by dissolution of lignin and hemicellulose between the cellulose microfibrils. The fibers become more accessible for hydrolysis by enzymes. When the sugars in lignocellulosics are used as feedstock for fermentation, the process to open up the cell wall structure is often called "pretreatment." Pretreatment can significantly impact the production cost of lignocellulosic ethanol.

One of the most challenging technical obstacles for cellulose has been its recalcitrance towards hydrolysis for glucose production. Because of the high quantity of enzymes typically required, the enzyme cost can be a tremendous burden on the overall cost to turn cellulose into glucose for fermentation. Cellulose can be made to be reactive by subjecting biomass to severe chemistry, but that would jeopardize not only its integrity for other potential uses but also the yields of hemicellulose and lignin.

Many types of pretreatment have been studied. A common chemical pretreatment process employs a dilute acid, usually sulfuric acid, to hydrolyze and extract hemicellulose sugars and some lignin. A common physical pretreatment process employs steam explosion to mechanically disrupt the cellulose fibers and promote some separation of hemicellulose and lignin. Combinations of chemical and physical pretreatments are possible, such as acid pretreatment coupled with mechanical refining.

Pretreatment prepares the biomass for enzymatic hydrolysis, i.e. the depolymerization of sugar oligomers to sugar monomers, catalyzed by enzymes such as cellulases. Typically, enzymatic hydrolysis is slow and takes several days to complete. Due to the long hydrolysis time, and the moderate temperature and pH employed, bacterial or yeast growth can contaminate the system. Such contamination can consume sugars produced by hydrolysis, produce problematic byproducts, and interfere with cellulose hydrolysis, for example. Improved processes are desired to avoid or reduce contamination during enzymatic hydrolysis of cellulose.

SUMMARY

The present invention addresses the aforementioned needs in the art.

Some variations provide a method of enzymatically converting biomass-derived cellulose to glucose, the method comprising exposing the biomass-derived cellulose to (i) cellulase enzymes, to hydrolyze the cellulose to glucose; and (ii) an external (i.e., not derived from the starting biomass) sulfur-containing compound, to deter bacterial and/or yeast contamination during cellulose hydrolysis.

In some embodiments, the sulfur-containing compound includes sulfur dioxide. In these or other embodiments, the sulfur-containing compound includes lignosulfonates. When the sulfur-containing compound includes lignosulfonates, the lignosulfonates may also function as an enzyme surfactant to assist hydrolysis, in addition to deterring bacterial and/or yeast growth/contamination.

In some embodiments, the biomass-derived cellulose is obtained from AVAP® biomass fractionation. When the AVAP® biomass fractionation employs sulfur dioxide, the sulfur dioxide, or a derivative thereof, may be employed as the sulfur-containing compound during the cellulose hydrolysis. In certain embodiments, lignosulfonic acid is employed as the sulfur-containing compound during the cellulose hydrolysis. The lignosulfonic acid may be obtained by reaction between the sulfur dioxide and lignin contained in the same biomass from which biomass-derived cellulose is derived. Or, the lignosulfonic acid may be introduced from another source.

In some embodiments, the biomass-derived cellulose is obtained from a GREEN POWER+® biomass pretreatment process. When the GREEN POWER+® biomass pretreatment process employs sulfur dioxide, the sulfur dioxide, or a derivative thereof, may be employed as the sulfur-containing compound during the cellulose hydrolysis.

The sulfur-containing compound may be present in solution during the cellulose hydrolysis at a concentration from about 10 ppm to about 1 wt %, such as from about 10 ppm to about 1000 ppm, for example.

The method further comprises, in some embodiments, fermenting the glucose to a fermentation product. The sulfur-containing compound may be removed prior to the fermenting. Alternatively, or additionally, the sulfur-containing compound may be removed following the fermenting.

Other variations of the invention provide a process for producing a fermentation product from cellulosic biomass, the process comprising:

(a) in a digestor, fractionating a feedstock comprising lignocellulosic biomass in the presence of a solvent for lignin, a hydrolysis catalyst, and water, to produce a liquor containing hemicellulose, cellulose-rich solids, and lignin;

(b) substantially separating the cellulose-rich solids from the liquor;

(c) hydrolyzing the hemicellulose contained in the liquor to produce fermentable hemicellulosic monomers;

(d) enzymatically converting cellulose-rich solids to glucose, comprising exposing the cellulose-rich solids to (i) cellulase enzymes, to hydrolyze cellulose to glucose; and (ii) an external sulfur-containing compound, to deter bacterial and/or yeast contamination during cellulose hydrolysis; and (e) fermenting at least a portion of the glucose and optionally the fermentable hemicellulosic monomers to a fermentation product.

The solvent for lignin may comprise an oxygenated hydrocarbon, $C_1$-$C_8$ aliphatic or aromatic alcohol, aliphatic or aromatic hydrocarbon, organic acid, inorganic acid, ionic liquid, or combination thereof.

The hydrolysis catalyst in step (a) may be selected from the group consisting of sulfur dioxide, sulfur trioxide, sulfurous acid, sulfuric acid, sulfonic acid, lignosulfonic acid, elemental sulfur, polysulfides, and combinations or derivatives thereof. In some embodiments, the hydrolysis catalyst is sulfur dioxide.

In some embodiments, hydrolyzing in step (c) utilizes the hydrolysis catalyst from step (a), or a reaction product thereof. For example, when the hydrolysis catalyst is sulfur dioxide, a reaction product of lignosulfonic acid may be employed during step (c).

In some embodiments, the sulfur-containing compound in step (d) is, or includes, the hydrolysis catalyst from step (a), or a reaction product thereof. For example, when the hydrolysis catalyst is sulfur dioxide, a reaction product of lignosulfonic acid or lignosulfonate may serve as all or some of the sulfur-containing compound in step (d).

The fermentation product may include an organic acid selected from the group consisting of formic acid, acetic acid, oxalic acid, lactic acid, propionic acid, 3-hydroxypropionic acid, malonic acid, aspartic acid, fumaric acid, malic acid, succinic acid, glutaric acid, adipic acid, citric acid, itaconic acid, levulinic acid, ascorbic acid, gluconic acid, kojic acid, threonine, glutamic acid, proline, lysine, alanine, serine, and any isomers, derivatives, or combinations thereof.

The fermentation product may include an oxygenated compound selected from the group consisting of ethanol, propanol, butanol, pentanol, hexanol, heptanol, octanol, glycerol, sorbitol, propanediol, butanediol, butanetriol, pentanediol, hexanediol, acetone, acetoin, butyrolactone, 3-hydroxybutyrolactone, and any isomers, derivatives, or combinations thereof.

The glucose may be fermented to a first fermentation product while the fermentable hemicellulosic monomers are fermented to a second fermentation product. Or, the fermentation products may be the same. In other embodiments, glucose and/or hemicellulosic monomers are recovered for other purposes, such as chemical conversion, or for sale.

In some embodiments, a portion of the fermentation product is recycled to step (a) for use as the solvent for lignin. Some processes include recovering the lignin, lignosulfonates, or both of these.

The sulfur-containing compound may be present in solution during the cellulose hydrolysis at a concentration from about 10 ppm to about 1 wt %, such as from about 10 ppm to about 1000 ppm. The sulfur-containing compound may be removed prior to, during, and/or following the fermenting step(s).

DETAILED DESCRIPTION OF SOME EMBODIMENTS

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with any accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. All composition numbers and ranges based on percentages are weight percentages, unless indicated otherwise. All ranges of numbers or conditions are meant to encompass any specific value contained within the range, rounded to any suitable decimal point.

Unless otherwise indicated, all numbers expressing parameters, reaction conditions, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" limits the scope of a claim to the specified elements or method steps, plus those that do not materially affect the basis and novel characteristic(s) of the claimed subject matter.

With respect to the terms "comprising," "consisting of" and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

Some variations are premised on the concept of introducing sulfur dioxide ($SO_2$), lignosulfonates, or another sulfur-containing compound in enzymatic hydrolysis to deter bacterial and yeast contamination during hydrolysis. When biomass fractionation employs $SO_2$, some amount of residual $SO_2$ from fractionation may be allowed to pass through to the enzymatic hydrolysis to sterilize the solution. The $SO_2$ may also mildly assist cellulose hydrolysis, i.e., act as an acid catalyst. The $SO_2$ may also functionalize lignin present on the cellulose surface and/or present as or in separate particles, so that the lignin becomes a surfactant in situ. The $SO_2$ or other sulfur-containing compounds can be then removed in the beer column via a condenser, for example.

Certain exemplary embodiments of the invention will now be described. These embodiments are not intended to limit the scope of the invention as claimed. The order of steps may be varied, some steps may be omitted, and/or other steps may be added. Reference herein to first step, second step, etc. is for illustration purposes only.

Some variations provide a method of enzymatically converting biomass-derived cellulose to glucose, the method comprising exposing the biomass-derived cellulose to (i) cellulase enzymes, to hydrolyze the cellulose to glucose; and (ii) an external (i.e., not derived from the starting biomass) sulfur-containing compound, to deter bacterial and/or yeast contamination during cellulose hydrolysis. The sulfur-containing compound may function as an antiseptic agent, sanitizing agent, antimicrobial compound, antioxidant, or antibiotic during cellulose hydrolysis.

The sulfur-containing compound may be selected from the group consisting of sulfur dioxide, sulfur trioxide, sulfurous acid, sulfuric acid, sulfonic acid, lignosulfonic acid, elemental sulfur, polysulfides, and combinations or derivatives thereof.

In some embodiments, the sulfur-containing compound includes sulfur dioxide. In these or other embodiments, the sulfur-containing compound includes lignosulfonates. When the sulfur-containing compound includes lignosulfonates, the lignosulfonates may also function as an enzyme surfactant to assist hydrolysis, in addition to deterring bacterial and/or yeast growth/contamination.

In some embodiments, the biomass-derived cellulose is obtained from AVAP® biomass fractionation. When the AVAP® biomass fractionation employs sulfur dioxide, the sulfur dioxide, or a derivative thereof, may be employed as the sulfur-containing compound during the cellulose hydrolysis. In certain embodiments, lignosulfonic acid is employed as the sulfur-containing compound during the cellulose hydrolysis. The lignosulfonic acid may be obtained by reaction between the sulfur dioxide and lignin contained in the same biomass from which biomass-derived cellulose is derived. Or, the lignosulfonic acid may be introduced from another source.

In some embodiments, the biomass-derived cellulose is obtained from GREEN POWER+® biomass pretreatment process or GP3+® biomass pretreatment process. When the GREEN POWER+® biomass pretreatment process employs sulfur dioxide, the sulfur dioxide, or a derivative thereof, may be employed as the sulfur-containing compound during the cellulose hydrolysis.

The sulfur-containing compound may be present in solution during the cellulose hydrolysis at a concentration from about 5 ppm to about 5 wt %, such as from about 10 ppm to about 1 wt %, or about 10, 20, 30, 50, 75, 100, 200, 300, 400, 500, 600, 700, 800, 900, or 1000 ppm, for example.

The method further comprises, in some embodiments, fermenting the glucose to a fermentation product. The sulfur-containing compound may be removed prior to the fermenting. Alternatively, or additionally, the sulfur-containing compound may be removed following the fermenting.

Other variations of the invention provide a process for producing a fermentation product from cellulosic biomass, the process comprising:

(a) in a digestor, fractionating a feedstock comprising lignocellulosic biomass in the presence of a solvent for lignin, a hydrolysis catalyst, and water, to produce a liquor containing hemicellulose, cellulose-rich solids, and lignin;

(b) substantially separating the cellulose-rich solids from the liquor;

(c) hydrolyzing the hemicellulose contained in the liquor to produce fermentable hemicellulosic monomers;

(d) enzymatically converting cellulose-rich solids to glucose, comprising exposing the cellulose-rich solids to (i) cellulase enzymes, to hydrolyze cellulose to glucose; and (ii) an external sulfur-containing compound, to deter bacterial and/or yeast contamination during cellulose hydrolysis; and (e) fermenting at least a portion of the glucose and optionally the fermentable hemicellulosic monomers to a fermentation product.

The solvent for lignin may comprise an oxygenated hydrocarbon, $C_1$-$C_8$ aliphatic or aromatic alcohol, aliphatic or aromatic hydrocarbon, organic acid, inorganic acid, ionic liquid, or combination thereof.

The hydrolysis catalyst in step (a) may be selected from the group consisting of sulfur dioxide, sulfur trioxide, sulfurous acid, sulfuric acid, sulfonic acid, lignosulfonic acid, elemental sulfur, polysulfides, and combinations or derivatives thereof. In some embodiments, the hydrolysis catalyst is sulfur dioxide.

In some embodiments, hydrolyzing in step (c) utilizes the hydrolysis catalyst from step (a), or a reaction product thereof. For example, when the hydrolysis catalyst is sulfur dioxide, a reaction product of lignosulfonic acid may be employed during step (c).

In some embodiments, the sulfur-containing compound in step (d) is, or includes, the hydrolysis catalyst from step (a), or a reaction product thereof. For example, when the hydrolysis catalyst is sulfur dioxide, a reaction product of lignosulfonic acid or lignosulfonate may serve as all or some of the sulfur-containing compound in step (d).

The fermentation product may include an organic acid selected from the group consisting of formic acid, acetic acid, oxalic acid, lactic acid, propionic acid, 3-hydroxypropionic acid, malonic acid, aspartic acid, fumaric acid, malic acid, succinic acid, glutaric acid, adipic acid, citric acid, itaconic acid, levulinic acid, ascorbic acid, gluconic acid, kojic acid, threonine, glutamic acid, proline, lysine, alanine, serine, and any isomers, derivatives, or combinations thereof.

The fermentation product may include an oxygenated compound selected from the group consisting of ethanol, propanol, butanol, pentanol, hexanol, heptanol, octanol, glycerol, sorbitol, propanediol, butanediol, butanetriol, pentanediol, hexanediol, acetone, acetoin, butyrolactone, 3-hydroxybutyrolactone, and any isomers, derivatives, or combinations thereof.

The glucose may be fermented to a first fermentation product while the fermentable hemicellulosic monomers are fermented to a second fermentation product. Or, the fermentation products may be the same. In other embodiments, glucose and/or hemicellulosic monomers are recovered for other purposes, such as chemical conversion, or for sale.

In some embodiments, a portion of the fermentation product is recycled to step (a) for use as the solvent for lignin. Some processes include recovering the lignin, lignosulfonates, or both of these.

The sulfur-containing compound may be present in solution during the cellulose hydrolysis at a concentration from about 10 ppm to about 1 wt %, such as from about 10 ppm to about 1000 ppm. The sulfur-containing compound may be removed prior to, during, and/or following the fermenting step(s).

The biomass feedstock may be selected from hardwoods, softwoods, forest residues, industrial wastes, pulp and paper wastes, consumer wastes, or combinations thereof. Some embodiments utilize agricultural residues, which include lignocellulosic biomass associated with food crops, annual grasses, energy crops, or other annually renewable feedstocks. Exemplary agricultural residues include, but are not limited to, corn stover, corn fiber, wheat straw, sugarcane bagasse, sugarcane straw, rice straw, oat straw, barley straw, miscanthus, energy cane straw/residue, or combinations thereof.

As used herein, "lignocellulosic biomass" means any material containing cellulose and lignin. Lignocellulosic biomass may also contain hemicellulose. Mixtures of one or more types of biomass can be used. In some embodiments, the biomass feedstock comprises both a lignocellulosic component (such as one described above) in addition to a sucrose-containing component (e.g., sugarcane or energy cane) and/or a starch component (e.g., corn, wheat, rice, etc.).

Various moisture levels may be associated with the starting biomass. The biomass feedstock need not be, but may be, relatively dry. In general, the biomass is in the form of a particulate or chip, but particle size is not critical in this invention.

The solvent for lignin preferably facilitates a higher mass transfer rate of the sulfur dioxide into the lignocellulosic biomass, compared to the mass transfer rate of sulfur dioxide into the lignocellulosic biomass with water alone. For example, ethanol facilitates better $SO_2$ mass transfer because ethanol (with dissolved $SO_2$) is able to penetrate into biomass pores more efficiently than water.

In some embodiments, the solvent for lignin comprises an oxygenated hydrocarbon, such as an aliphatic alcohol which may be a $C_1$-$C_8$ alcohol, for example, or an aromatic alcohol, such as phenol. In some embodiments, the solvent for lignin comprises an aliphatic or aromatic hydrocarbon.

In some embodiments, the solvent for lignin comprises an organic acid. For example, without limitation, the organic acid may be selected from the group consisting of acetic acid, formic acid, oxalic acid, lactic acid, propionic acid, 3-hydroxypropionic acid, malonic acid, aspartic acid, fumaric acid, malic acid, succinic acid, glutaric acid, adipic acid, citric acid, itaconic acid, levulinic acid, ascorbic acid, gluconic acid, kojic acid, and combinations thereof.

In these or other embodiments, the solvent for lignin comprises an inorganic acid, such as concentrated phosphoric acid. In certain embodiments, the solvent for lignin comprises an ionic liquid.

The process may further include recovering the lignin, lignosulfonates, or both of these. Recovery of lignin typically involves removal of solvent, dilution with water, adjustment of temperature or pH, addition of an acid or base, or some combination thereof.

The sulfur dioxide may be present in a liquid-phase concentration of about 1 wt % to about 50 wt %, or about 6 wt % to about 30 wt %, or about 9 wt % to about 20 wt %, in various embodiments.

The process typically includes washing of the cellulose-rich solids, which preferably includes countercurrent washing of the cellulose-rich solids.

Hydrolyzing the hemicellulose contained in the liquor may be catalyzed by lignosulfonic acids that are generated during step (a).

The fermentation product may include an organic acid, such as (but not limited to) organic acids selected from the group consisting of formic acid, acetic acid, oxalic acid, lactic acid, propionic acid, 3-hydroxypropionic acid, malonic acid, aspartic acid, fumaric acid, malic acid, succinic acid, glutaric acid, adipic acid, citric acid, itaconic acid, levulinic acid, ascorbic acid, gluconic acid, kojic acid, threonine, glutamic acid, proline, lysine, alanine, serine, and any isomers, derivatives, or combinations thereof. In certain embodiments, the organic acid is succinic acid. "Derivatives" may be salts of these acids, or esters, or reaction products to convert the acid to another molecule that is not an acid. For example, when the fermentation product is succinic acid, it may be further converted to 1,4-butanediol as a derivative using known hydrotreating chemistry.

The fermentation product may include an oxygenated compound, such as (but not limited to) oxygenated compounds selected from the group consisting of ethanol, propanol, butanol, pentanol, hexanol, heptanol, octanol, glycerol, sorbitol, propanediol, butanediol, butanetriol, pentanediol, hexanediol, acetone, acetoin, butyrolactone, 3-hydroxybutyrolactone, and any isomers, derivatives, or combinations thereof.

In some embodiments, the oxygenated compound is a $C_3$ or higher alcohol or diol, such as 1-butanol, isobutanol, 1,4-butanediol, 2,3-butanediol, or mixtures thereof.

The fermentation product may include a hydrocarbon, such as isoprene, farnasene, and related compounds.

Multiple fermentation products may be produced in a single fermentor, in co-product production or as a result of byproducts due to contaminant microorganisms. For example, during fermentation to produce lactic acid, ethanol is a common byproduct due to contamination (and vice-versa).

Multiple fermentation products may be produced in separate fermentors. In some embodiments, a first fermentation product, such as an organic acid, is produced from glucose (hydrolyzed cellulose) while a second fermentation product, such as ethanol, is produced from hemicellulose sugars. Or, in some embodiments, different fermentations are directed to portions of feedstock having varying particle size, crystallinity, or other properties.

In some embodiments, different fermentations are directed to portions of whole biomass that is separated into a starch or sucrose-rich fraction, and a cellulose-rich fraction (for example, corn starch/stover or sugarcane syrup/bagasse). For example, from raw corn, an organic acid or polyol may be produced from starch (hydrolyzed to glucose), the same or a different organic acid or polyol may be produced from cellulose (hydrolyzed to glucose), and ethanol may be produced from hemicellulose sugars. Many variations are possible, as will be recognized by a person skilled in the biorefinery art, in view of the present disclosure.

The solvent for lignin may include a component that is the same as the fermentation product. In some embodiments, the solvent for lignin is the same compound as the fermentation product. For example, the solvent and the fermentation product may be 1-butanol, or lactic acid, succinic acid, or 1,4-butanediol. Of course, other solvents may be present even when these products are utilized as solvents or co-solvents. Beneficially, a portion of the fermentation product may be recycled to step (a) for use as the solvent for lignin.

In some embodiments, the fermentation product includes an enzymatically isomerized variant of at least a portion of the fermentable sugars. For example, the enzymatically isomerized variant may include fructose which is isomerized from glucose. In some embodiments, glucose, which is normally D-glucose, is isomerized with enzymes to produce L-glucose.

In some embodiments, the fermentation product includes one or more proteins, amino acids, enzymes, or microorganisms. Such fermentation products may be recovered and used within the process; for example, cellulase or hemicellulase enzymes may be used for hydrolyzing cellulose-rich solids or hemicellulose oligomers.

Some variations are premised on the recognition that the clean cellulose produced in these processes may be not only hydrolyzed to glucose, but also recovered as a cellulose pulp product, intermediate, or precursor (such as for nanocellulose). Also, the initial fractionation step (in the digestor) does not necessarily employ $SO_2$ as the hydrolysis catalyst, although $SO_2$ is a preferred hydrolysis catalyst.

In some embodiments, the hydrolysis catalyst is present in a liquid-phase concentration of about 1 wt % to about 50 wt % during step (a), such as about 6 wt % to about 30 wt %, or about 9 wt % to about 20 wt %. The hydrolysis catalyst in step (a) may be selected from the group consisting of sulfur dioxide, sulfur trioxide, sulfurous acid, sulfuric acid, sulfonic acid, lignosulfonic acid, elemental sulfur, polysulfides, and combinations or derivatives thereof.

In some embodiments, the hydrolyzing of hemicelluloses utilizes the hydrolysis catalyst from step (a), or a reaction product thereof. For example, in certain embodiments the hydrolysis catalyst is sulfur dioxide and the reaction product is lignosulfonic acid. In other embodiments, the hydrolyzing utilizes hemicellulase enzymes as hydrolysis catalyst.

In some embodiments, the solvent for lignin also contains the functionality of a hydrolysis catalyst, i.e. there is not a separate hydrolysis catalyst present. In particular, when the solvent for lignin is an organic acid, it may also function as the hydrolysis catalyst.

In some embodiments, the process further comprises saccharifying at least some of the cellulose-rich solids to produce glucose. In these or other embodiments, the process further comprises recovering or further treating or reacting at least some of the cellulose-rich solids as a pulp precursor or product. When glucose is produced (by acid or enzyme hydrolysis of the cellulose), that glucose may form part of the fermentable sugars, either separately from the hemicellulose-derived fermentable sugars, or as a combined sugar stream.

In some embodiments, the fermentation product is ethanol, 1-butanol, succinic acid, 1,4-butanediol, or a combination thereof. In some embodiments, the solvent for lignin includes a component that is the same as the fermentation product, or is the same compound as the fermentation product. Thus a portion of the fermentation product may be recycled to step (a) for use as the solvent for lignin.

Reaction conditions and operation sequences may vary widely. Some embodiments employ conditions described in U.S. Pat. No. 8,030,039, issued Oct. 4, 2011; U.S. Pat. No. 8,038,842, issued Oct. 11, 2011; or U.S. Pat. No. 8,268,125, issued Sep. 18, 2012. Each of these commonly owned patents is hereby incorporated by reference herein in its entirety. In some embodiments, the process is a variation of the AVAP® fractionation process which is commonly owned with the assignee of this patent application.

In some embodiments, a first process step is "cooking" (equivalently, "digesting") which fractionates the three lignocellulosic material components (cellulose, hemicellulose, and lignin) to allow easy downstream removal. Specifically, hemicelluloses are dissolved and over 50% are completely hydrolyzed; cellulose is separated but remains resistant to hydrolysis; and part of the lignin is sulfonated into water-soluble lignosulfonates.

The lignocellulosic material is processed in a solution (cooking liquor) of aliphatic alcohol, water, and sulfur dioxide. The cooking liquor preferably contains at least 10 wt %, such as at least 20 wt %, 30 wt %, 40 wt %, or 50 wt % of a solvent for lignin. For example, the cooking liquor may contain about 30-70 wt % solvent, such as about 50 wt % solvent. The solvent for lignin may be an aliphatic alcohol, such as methanol, ethanol, 1-propanol, 2-propanol, 1-butanol, 2-butanol, isobutanol, 1-pentanol, 1-hexanol, or cyclohexanol. The solvent for lignin may be an aromatic alcohol, such as phenol or cresol. Other lignin solvents are possible, such as (but not limited to) glycerol, methyl ethyl ketone, or diethyl ether. Combinations of more than one solvent may be employed.

Preferably, enough solvent is included in the extractant mixture to dissolve the lignin present in the starting material. The solvent for lignin may be completely miscible, partially miscible, or immiscible with water, so that there may be more than one liquid phase. Potential process advantages arise when the solvent is miscible with water, and also when the solvent is immiscible with water. When the solvent is water-miscible, a single liquid phase forms, so mass transfer of lignin and hemicellulose extraction is enhanced, and the downstream process must only deal with one liquid stream. When the solvent is immiscible in water, the extractant mixture readily separates to form liquid phases, so a distinct separation step can be avoided or simplified. This can be advantageous if one liquid phase contains most of the lignin and the other contains most of the hemicellulose sugars, as this facilitates recovering the lignin from the hemicellulose sugars.

The cooking liquor preferably contains sulfur dioxide and/or sulfurous acid ($H_2SO_3$). The cooking liquor preferably contains $SO_2$, in dissolved or reacted form, in a concentration of at least 3 wt %, preferably at least 6 wt %, more preferably at least 8 wt %, such as about 9 wt %, 10 wt %, 11 wt %, 12 wt %, 13 wt %, 14 wt %, 15 wt %, 20 wt %, 25 wt %, 30 wt % or higher. The cooking liquor may also contain one or more species, separately from $SO_2$, to adjust the pH. The pH of the cooking liquor is typically about 4 or less.

Sulfur dioxide is a preferred acid catalyst, because it can be recovered easily from solution after hydrolysis. The majority of the $SO_2$ from the hydrolysate may be stripped and recycled back to the reactor. A selected amount of $SO_2$ may be allowed to pass through to enzymatic hydrolysis, according to the principles taught herein. Recovery and recycling translates to less lime required compared to neutralization of comparable sulfuric acid, less solids to dispose of, and less separation equipment. The increased efficiency owing to the inherent properties of sulfur dioxide mean that less total acid or other catalysts may be required. This has cost advantages, since sulfuric acid can be expensive. Additionally, and quite significantly, less acid usage also will translate into lower costs for a base (e.g., lime) to increase the pH following hydrolysis, for downstream operations. Furthermore, less acid and less base will also mean substantially less generation of waste salts (e.g., gypsum) that may otherwise require disposal.

In some embodiments, an additive may be included in amounts of about 0.1 wt % to 10 wt % or more to increase cellulose viscosity. Exemplary additives include ammonia, ammonia hydroxide, urea, anthraquinone, magnesium oxide, magnesium hydroxide, sodium hydroxide, and their derivatives.

The cooking is performed in one or more stages using batch or continuous digestors. Solid and liquid may flow cocurrently or countercurrently, or in any other flow pattern that achieves the desired fractionation. The cooking reactor may be internally agitated, if desired.

Depending on the lignocellulosic material to be processed, the cooking conditions are varied, with temperatures from about 65° C. to 175° C., for example 75° C., 85° C., 95° C., 105° C., 115° C., 125° C., 130° C., 135° C., 140° C., 145° C., 150° C., 155° C., 165° C. or 170° C., and corresponding pressures from about 1 atmosphere to about 15 atmospheres in the liquid or vapor phase. The cooking time of one or more stages may be selected from about 15 minutes to about 720 minutes, such as about 30, 45, 60, 90, 120, 140, 160, 180, 250, 300, 360, 450, 550, 600, or 700 minutes. Generally, there is an inverse relationship between the temperature used during the digestion step and the time needed to obtain good fractionation of the biomass into its constituent parts.

The cooking liquor to lignocellulosic material ratio may be selected from about 1 to about 10, such as about 2, 3, 4, 5, or 6. In some embodiments, biomass is digested in a pressurized vessel with low liquor volume (low ratio of cooking liquor to lignocellulosic material), so that the cooking space is filled with ethanol and sulfur dioxide vapor in equilibrium with moisture. The cooked biomass is washed in alcohol-rich solution to recover lignin and dissolved hemicelluloses, while the remaining pulp is further processed. In some embodiments, the process of fractionating lignocellulosic material comprises vapor-phase cooking of lignocellulosic material with aliphatic alcohol (or other solvent for lignin), water, and sulfur dioxide. See, for example, U.S. Pat. Nos. 8,038,842 and 8,268,125 which are incorporated by reference herein.

A portion or all of the sulfur dioxide may be present as sulfurous acid in the extract liquor. In certain embodiments, sulfur dioxide is generated in situ by introducing sulfurous acid, sulfite ions, bisulfite ions, combinations thereof, or a salt of any of the foregoing. Excess sulfur dioxide, following hydrolysis, may be recovered and reused.

In some embodiments, sulfur dioxide is saturated in water (or aqueous solution, optionally with an alcohol) at a first temperature, and the hydrolysis is then carried out at a second, generally higher, temperature. In some embodiments, sulfur dioxide is sub-saturated. In some embodiments, sulfur dioxide is super-saturated. In some embodiments, sulfur dioxide concentration is selected to achieve a certain degree of lignin sulfonation, such as 1%, 2%, 3%, 4%, 5%, 6%, 7%, 8%, 9%, or 10% sulfur content. $SO_2$ reacts chemically with lignin to form stable lignosulfonic acids which may be present both in the solid and liquid phases.

The concentration of sulfur dioxide, additives, and aliphatic alcohol (or other solvent) in the solution and the time of cook may be varied to control the yield of cellulose and hemicellulose in the pulp. The concentration of sulfur dioxide and the time of cook may be varied to control the yield of lignin versus lignosulfonates in the hydrolysate. In some embodiments, the concentration of sulfur dioxide, temperature, and the time of cook may be varied to control the yield of fermentable sugars.

Once the desired amount of fractionation of both hemicellulose and lignin from the solid phase is achieved, the liquid and solid phases are separated. Conditions for the separation may be selected to minimize the reprecipitation of the extracted lignin on the solid phase. This is favored by conducting separation or washing at a temperature of at least the glass-transition temperature of lignin (about 120° C.).

The physical separation can be accomplished either by transferring the entire mixture to a device that can carry out the separation and washing, or by removing only one of the phases from the reactor while keeping the other phase in place. The solid phase can be physically retained by appropriately sized screens through which liquid can pass. The solid is retained on the screens and can be kept there for successive solid-wash cycles. Alternately, the liquid may be retained and solid phase forced out of the reaction zone, with centrifugal or other forces that can effectively transfer the solids out of the slurry. In a continuous system, countercurrent flow of solids and liquid can accomplish the physical separation.

The recovered solids normally will contain a quantity of lignin and sugars, some of which can be removed easily by washing. The washing-liquid composition can be the same as or different than the liquor composition used during fractionation. Multiple washes may be performed to increase effectiveness. Preferably, one or more washes are performed with a composition including a solvent for lignin, to remove additional lignin from the solids, followed by one or more washes with water to displace residual solvent and sugars from the solids. Recycle streams, such as from solvent-recovery operations, may be used to wash the solids.

After separation and washing as described, a solid phase and at least one liquid phase are obtained. The solid phase contains substantially undigested cellulose. A single liquid phase is usually obtained when the solvent and the water are miscible in the relative proportions that are present. In that case, the liquid phase contains, in dissolved form, most of the lignin originally in the starting lignocellulosic material, as well as soluble monomeric and oligomeric sugars formed in the hydrolysis of any hemicellulose that may have been present. Multiple liquid phases tend to form when the solvent and water are wholly or partially immiscible. The lignin tends to be contained in the liquid phase that contains most of the solvent. Hemicellulose hydrolysis products tend to be present in the liquid phase that contains most of the water.

In some embodiments, hydrolysate from the cooking step is subjected to pressure reduction. Pressure reduction may be done at the end of a cook in a batch digestor, or in an external flash tank after extraction from a continuous digestor, for example. The flash vapor from the pressure reduction may be collected into a cooking liquor make-up vessel. The flash vapor contains substantially all the unreacted sulfur dioxide which may be directly dissolved into new cooking liquor. The cellulose is then removed to be washed and further treated as desired.

A process washing step recovers the hydrolysate from the cellulose. The washed cellulose is pulp that may be used for various purposes (e.g., paper or nanocellulose production). The weak hydrolysate from the washer continues to the final reaction step; in a continuous digestor this weak hydrolysate may be combined with the extracted hydrolysate from the external flash tank. In some embodiments, washing and/or separation of hydrolysate and cellulose-rich solids is conducted at a temperature of at least about 100° C., 110° C., or 120° C. The washed cellulose may also be used for glucose production via cellulose hydrolysis with enzymes or acids.

In another reaction step, the hydrolysate may be further treated in one or multiple steps to hydrolyze the oligomers into monomers. This step may be conducted before, during, or after the removal of solvent and sulfur dioxide. The solution may or may not contain residual solvent (e.g. alcohol). In some embodiments, sulfur dioxide is added or allowed to pass through to this step, to assist hydrolysis. In these or other embodiments, an acid such as sulfurous acid or sulfuric acid is introduced to assist with hydrolysis. In some embodiments, the hydrolysate is autohydrolyzed by heating under pressure. In some embodiments, no additional acid is introduced, but lignosulfonic acids produced during the initial cooking are effective to catalyze hydrolysis of hemicellulose oligomers to monomers. In various embodiments, this step utilizes sulfur dioxide, sulfurous acid, sulfuric acid at a concentration of about 0.01 wt % to 30 wt %, such as about 0.05 wt %, 0.1 wt %, 0.2 wt %, 0.5 wt %, 1 wt %, 2 wt %, 5 wt %, 10 wt %, or 20 wt %. This step may be carried out at a temperature from about 100° C. to 220° C., such as about 110° C., 120° C., 130° C., 140° C., 150° C., 160° C., 170° C., 180° C., 190° C., 200° C., or 210° C. Heating may be direct or indirect to reach the selected temperature.

The reaction step produces fermentable sugars which can then be concentrated by evaporation to a fermentation feedstock. Concentration by evaporation may be accomplished before, during, or after the treatment to hydrolyze oligomers. The final reaction step may optionally be followed by steam stripping of the resulting hydrolysate to remove and recover sulfur dioxide and alcohol, and for removal of potential fermentation-inhibiting side products. The evaporation process may be under vacuum or pressure, from about −0.1 atmospheres to about 10 atmospheres, such as about 0.1 atm, 0.3 atm, 0.5 atm, 1.0 atm, 1.5 atm, 2 atm, 4 atm, 6 atm, or 8 atm.

Recovering and recycling the sulfur dioxide may utilize separations such as, but not limited to, vapor-liquid disengagement (e.g. flashing), steam stripping, extraction, or combinations or multiple stages thereof. Various recycle ratios may be practiced, such as about 0.1, 0.2, 0.3, 0.4, 0.5, 0.6, 0.7, 0.8, 0.9, 0.95, or more. In some embodiments, about 90-99% of initially charged $SO_2$ is readily recovered by distillation from the liquid phase, with the remaining 1-10% (e.g., about 3-5%) of the $SO_2$ primarily bound to dissolved lignin in the form of lignosulfonates.

In a preferred embodiment, the evaporation step utilizes an integrated alcohol stripper and evaporator. Evaporated vapor streams may be segregated so as to have different concentrations of organic compounds in different streams. Evaporator condensate streams may be segregated so as to have different concentrations of organic compounds in different streams. Alcohol may be recovered from the evaporation process by condensing the exhaust vapor and returning to the cooking liquor make-up vessel in the cooking step. Clean condensate from the evaporation process may be used in the washing step.

In some embodiments, an integrated alcohol stripper and evaporator system is employed, wherein aliphatic alcohol is removed by vapor stripping, the resulting stripper product stream is concentrated by evaporating water from the stream, and evaporated vapor is compressed using vapor compression and is reused to provide thermal energy.

The hydrolysate from the evaporation and final reaction step contains mainly fermentable sugars but may also contain lignin depending on the location of lignin separation in the overall process configuration. The hydrolysate may be concentrated to a concentration of about 5 wt % to about 60 wt % solids, such as about 10 wt %, 15 wt %, 20 wt %, 25 wt %, 30 wt %, 35 wt %, 40 wt %, 45 wt %, 50 wt % or 55 wt % solids. The hydrolysate contains fermentable sugars.

Fermentable sugars are defined as hydrolysis products of cellulose, galactoglucomannan, glucomannan, arabinoglucuronoxylans, arabinogalactan, and glucuronoxylans into their respective short-chained oligomers and monomer products, i.e., glucose, mannose, galactose, xylose, and arabinose. The fermentable sugars may be recovered in purified form, as a sugar slurry or dry sugar solids, for example. Any known technique may be employed to recover a slurry of sugars or to dry the solution to produce dry sugar solids.

In some embodiments, the fermentable sugars are fermented to produce biochemicals or biofuels such as (but by no means limited to) ethanol, isopropanol, acetone, 1-butanol, isobutanol, lactic acid, succinic acid, or any other fermentation products. Some amount of the fermentation product may be a microorganism or enzymes, which may be recovered if desired.

When the fermentation will employ bacteria, such as *Clostridia* bacteria, it is preferable to further process and condition the hydrolysate to raise pH and remove residual $SO_2$ and other fermentation inhibitors. The residual $SO_2$ (i.e., following removal of most of it by stripping) may be catalytically oxidized to convert residual sulfite ions to sulfate ions by oxidation. This oxidation may be accomplished by adding an oxidation catalyst, such as $FeSO4.7H_2O$, that oxidizes sulfite ions to sulfate ions. Preferably, the residual $SO_2$ is reduced to less than about 100 ppm, 50 ppm, 25 ppm, 10 ppm, 5 ppm, or 1 ppm.

In some embodiments, the process further comprises recovering the lignin as a co-product. The sulfonated lignin may also be recovered as a co-product. In certain embodiments, the process further comprises combusting or gasifying the sulfonated lignin, recovering sulfur contained in the sulfonated lignin in a gas stream comprising reclaimed sulfur dioxide, and then recycling the reclaimed sulfur dioxide for reuse.

The process lignin separation step is for the separation of lignin from the hydrolysate and can be located before or after the final reaction step and evaporation. If located after, then lignin will precipitate from the hydrolysate since alcohol has been removed in the evaporation step. The remaining water-soluble lignosulfonates may be precipitated by converting the hydrolysate to an alkaline condition (pH higher than 7) using, for example, an alkaline earth oxide, preferably calcium oxide (lime). The combined lignin and lignosulfonate precipitate may be filtered. The lignin and lignosulfonate filter cake may be dried as a co-product or burned or gasified for energy production. The hydrolysate from filtering may be recovered and sold as a concentrated sugar solution product or further processed in a subsequent fermentation or other reaction step.

Native (non-sulfonated) lignin is hydrophobic, while lignosulfonates are hydrophilic. Hydrophilic lignosulfonates may have less propensity to clump, agglomerate, and stick to surfaces. Even lignosulfonates that do undergo some condensation and increase of molecular weight, will still have an $HSO_3$ group that will contribute some solubility (hydrophilic).

In some embodiments, the soluble lignin precipitates from the hydrolysate after solvent has been removed in the evaporation step. In some embodiments, reactive lignosulfonates are selectively precipitated from hydrolysate using excess lime (or other base, such as ammonia) in the presence of aliphatic alcohol. In some embodiments, hydrated lime is used to precipitate lignosulfonates. In some embodiments, part of the lignin is precipitated in reactive form and the remaining lignin is sulfonated in water-soluble form.

The process fermentation and distillation steps are intended for the production of fermentation products, such as alcohols or organic acids. After removal of cooking chemicals and lignin, and further treatment (oligomer hydrolysis), the hydrolysate contains mainly fermentable sugars in water solution from which any fermentation inhibitors have been preferably removed or neutralized. The hydrolysate is fermented to produce dilute alcohol or organic acids, from 1 wt % to 20 wt % concentration. The dilute product is distilled or otherwise purified as is known in the art.

When alcohol is produced, such as ethanol, some of it may be used for cooking liquor makeup in the process cooking step. Also, in some embodiments, a distillation column stream, such as the bottoms, with or without evaporator condensate, may be reused to wash cellulose. In some embodiments, lime may be used to dehydrate product alcohol. Side products may be removed and recovered from the hydrolysate. These side products may be isolated by processing the vent from the final reaction step and/or the condensate from the evaporation step. Side products include furfural, hydroxymethyl furfural (HMF), methanol, acetic acid, and lignin-derived compounds, for example.

The cellulose-rich material is highly reactive in the presence of industrial cellulase enzymes that efficiently break the cellulose down to glucose monomers. It has been found experimentally that the cellulose-rich material, which generally speaking is highly delignified, rapidly hydrolyzes to glucose with relatively low quantities of enzymes. For example, the cellulose-rich solids may be converted to glucose with at least 80% yield within 24 hours at 50° C. and 2 wt % solids, in the presence of a cellulase enzyme mixture in an amount of no more than 15 filter paper units (FPU) per g of the solids. In some embodiments, this same conversion requires no more than 5 FPU per g of the solids.

The glucose may be fermented to an alcohol, an organic acid, or another fermentation product. The glucose may be used as a sweetener or isomerized to enrich its fructose content. The glucose may be used to produce baker's yeast. The glucose may be catalytically or thermally converted to various organic acids and other materials.

In some embodiments, the cellulose-rich material is further processed into one more cellulose products. Cellulose products include market pulp, dissolving pulp (also known as α-cellulose), fluff pulp, purified cellulose, paper, paper products, and so on. Further processing may include bleaching, if desired. Further processing may include modification of fiber length or particle size, such as when producing nanocellulose or nanofibrillated or microfibrillated cellulose. It is believed that the cellulose produced by this process is highly amenable to derivatization chemistry for cellulose derivatives and cellulose-based materials such as polymers.

When hemicellulose is present in the starting biomass, all or a portion of the liquid phase contains hemicellulose sugars and soluble oligomers. It is preferred to remove most of the lignin from the liquid, as described above, to produce a fermentation broth which will contain water, possibly some of the solvent for lignin, hemicellulose sugars, and various minor components from the digestion process. This fermentation broth can be used directly, combined with one or more other fermentation streams, or further treated. Further treatment can include sugar concentration by evaporation; addition of glucose or other sugars (optionally as obtained from cellulose saccharification); addition of various nutrients such as salts, vitamins, or trace elements; pH adjustment; and removal of fermentation inhibitors such as acetic acid and phenolic compounds. The choice of conditioning steps should be specific to the target product(s) and microorganism(s) employed.

In some embodiments, hemicellulose sugars are not fermented but rather are recovered and purified, stored, sold, or converted to a specialty product. Xylose, for example, can be converted into xylitol.

A lignin product can be readily obtained from a liquid phase using one or more of several methods. One simple technique is to evaporate off all liquid, resulting in a solid lignin-rich residue. This technique would be especially advantageous if the solvent for lignin is water-immiscible. Another method is to cause the lignin to precipitate out of solution. Some of the ways to precipitate the lignin include (1) removing the solvent for lignin from the liquid phase, but not the water, such as by selectively evaporating the solvent from the liquid phase until the lignin is no longer soluble; (2) diluting the liquid phase with water until the lignin is no longer soluble; and (3) adjusting the temperature and/or pH of the liquid phase. Methods such as centrifugation can then be utilized to capture the lignin. Yet another technique for removing the lignin is continuous liquid-liquid extraction to selectively remove the lignin from the liquid phase, followed by removal of the extraction solvent to recover relatively pure lignin.

Lignin produced in accordance with the invention can be used as a fuel. As a solid fuel, lignin is similar in energy content to coal. Lignin can act as an oxygenated component in liquid fuels, to enhance octane while meeting standards as a renewable fuel. The lignin produced herein can also be used as polymeric material, and as a chemical precursor for producing lignin derivatives. The sulfonated lignin may be sold as a lignosulfonate product, or burned for fuel value.

The present invention also provides systems configured for carrying out the disclosed processes, and compositions produced therefrom. Any stream generated by the disclosed processes may be partially or completed recovered, purified or further treated, and/or marketed or sold.

The present invention also provides one or more products, coproducts, and byproducts produced by a process as described. In preferred embodiments, a product comprises the fermentation product or a derivative thereof. In addition, an intermediate may be produced within a process, and recovered. For example, the intermediate may include purified fermentable sugars in dried form, crystallized form, pressed form, or slurried form.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A process for producing a fermentation product from cellulosic biomass, said process comprising:
   (a) in a digestor, fractionating a feedstock comprising lignocellulosic biomass in the presence of a solvent for lignin, a hydrolysis catalyst, and water, to produce a liquor containing hemicellulose, cellulose-rich solids, and lignin;
   (b) separating said cellulose-rich solids from said liquor;
   (c) hydrolyzing said hemicellulose contained in said liquor to produce fermentable hemicellulosic monomers;
   (d) enzymatically converting cellulose-rich solids to glucose, comprising exposing said cellulose-rich solids to: (i) cellulase enzymes, to hydrolyze cellulose to glucose; and (ii) an external sulfur-containing compound, to deter bacterial and/or yeast contamination during said enzymatically converting cellulose-rich solids to glucose; and
   (e) fermenting at least a portion of said glucose and optionally said fermentable hemicellulosic monomers to a fermentation product.

2. The process of claim 1, wherein said solvent for lignin comprises an oxygenated hydrocarbon, $C_1$-$C_8$ aliphatic or aromatic alcohol, aliphatic or aromatic hydrocarbon, organic acid, inorganic acid, ionic liquid, or combination thereof.

3. The process of claim 1, wherein said hydrolysis catalyst in step (a) is selected from the group consisting of sulfur dioxide, sulfur trioxide, sulfurous acid, sulfuric acid, sulfonic acid, lignosulfonic acid, elemental sulfur, polysulfides, and combinations or derivatives thereof.

4. The process of claim 1, wherein said sulfur-containing compound in step (d) is said hydrolysis catalyst from step (a), or a reaction product thereof.

5. The process of claim 4, wherein said hydrolysis catalyst is sulfur dioxide and wherein said reaction product is lignosulfonic acid or lignosulfonate.

6. The process of claim 1, wherein said fermentation product includes an organic acid selected from the group consisting of formic acid, acetic acid, oxalic acid, lactic acid, propionic acid, 3-hydroxypropionic acid, malonic acid, aspartic acid, fumaric acid, malic acid, succinic acid, glutaric acid, adipic acid, citric acid, itaconic acid, levulinic acid, ascorbic acid, gluconic acid, kojic acid, threonine, glutamic acid, proline, lysine, alanine, serine, and any isomers, derivatives, or combinations thereof.

7. The process of claim 1, wherein said fermentation product includes an oxygenated compound selected from the group consisting of ethanol, propanol, butanol, pentanol, hexanol, heptanol, octanol, glycerol, sorbitol, propanediol, butanediol, butanetriol, pentanediol, hexanediol, acetone, acetoin, butyrolactone, 3-hydroxybutyrolactone, and any isomers, derivatives, or combinations thereof.

8. The process of claim 1, wherein said sulfur-containing compound is present in solution during said cellulose hydrolysis at a concentration from about 10 ppm to about 1 wt %.

9. The process of claim 8, wherein said sulfur-containing compound is present in solution during said cellulose hydrolysis at a concentration from about 10 ppm to about 1000 ppm.

* * * * *